(12) United States Patent
Hobbs

(10) Patent No.: US 7,045,654 B2
(45) Date of Patent: May 16, 2006

(54) METHOD FOR THE ALKYLATION OF SALICYLIC ACID

(75) Inventor: Steven J. Hobbs, Wolcott, CT (US)

(73) Assignee: Crompton Corporation, Middlebury, CT (US)

( * ) Notice: Subject to any disclaimer, the term of this patent is extended or adjusted under 35 U.S.C. 154(b) by 87 days.

(21) Appl. No.: 10/691,390

(22) Filed: Oct. 21, 2003

(65) Prior Publication Data

US 2004/0127743 A1   Jul. 1, 2004

Related U.S. Application Data

(60) Provisional application No. 60/422,492, filed on Oct. 31, 2002.

(51) Int. Cl.
*C07C 65/10* (2006.01)

(52) U.S. Cl. .................................... 562/477

(58) Field of Classification Search ............... 562/477
See application file for complete search history.

(56) References Cited

U.S. PATENT DOCUMENTS

| | | | |
|---|---|---|---|
| 1,998,750 A | 4/1935 | Brunson et al. ............ 260/111 |
| 2,490,444 A | 12/1949 | Kooijman et al. .......... 260/521 |
| 2,865,956 A | 12/1958 | Ellis et al. .................. 260/504 |
| 3,337,616 A | 8/1967 | Kaeding et al. ............ 260/521 |
| 3,410,798 A | 11/1968 | Cohen ......................... 252/37.2 |
| 3,438,899 A | 4/1969 | Benoit, Jr. ................. 252/51.5 |
| 3,557,198 A | 1/1971 | Yakimik ..................... 260/521 |
| 3,704,315 A | 11/1972 | Strang |
| 3,853,956 A | 12/1974 | Schmerling ................. 260/473 |
| 3,884,949 A | 5/1975 | Eicke et al. ............... 260/429.3 |
| 4,060,535 A | 11/1977 | Cinco ......................... 260/414 |
| 4,544,491 A | 10/1985 | Tyson et al. ................ 210/772 |
| 4,810,398 A * | 3/1989 | Van Kruchten et al. .... 508/460 |
| 4,869,837 A * | 9/1989 | van Wijngaarden et al. ........................... 508/460 |
| 4,876,020 A * | 10/1989 | Zon et al. ................... 508/460 |
| 4,910,334 A | 3/1990 | Stuart et al. ................. 562/96 |
| 5,049,685 A | 9/1991 | Saito ........................... 556/132 |
| 5,225,588 A | 7/1993 | Senaratne et al. ........... 560/71 |
| 5,259,966 A | 11/1993 | Burke et al. .................. 252/18 |
| 5,415,792 A | 5/1995 | Campbell ..................... 252/18 |
| 5,434,293 A | 7/1995 | Campbell ..................... 560/71 |
| 5,451,331 A | 9/1995 | O'Connor et al. ............ 252/18 |
| 5,538,650 A | 7/1996 | Goto et al. .................. 508/331 |
| 5,652,203 A | 7/1997 | Asamori et al. ............ 508/460 |
| 5,734,078 A | 3/1998 | Feilden et al. .............. 562/477 |
| 5,792,735 A | 8/1998 | Cook et al. ................. 508/452 |
| 6,034,039 A | 3/2000 | Gomes et al. .............. 508/331 |
| 6,281,179 B1 | 8/2001 | Skinner et al. ............. 510/184 |
| 6,348,438 B1 | 2/2002 | Le Coent et al. ........... 508/332 |
| 6,417,148 B1 | 7/2002 | Skinner et al. ............. 510/184 |
| 6,429,178 B1 | 8/2002 | Skinner et al. ............. 510/184 |
| 6,429,179 B1 | 8/2002 | Skinner et al. ............. 510/184 |

FOREIGN PATENT DOCUMENTS

| | | |
|---|---|---|
| DE | 689600 | 3/1940 |
| DE | 269619 | 7/1989 |
| DE | 293108 | 8/1991 |
| EP | 0351052 | 1/1990 |
| EP | 0771782 A1 | 5/1997 |
| EP | 0771782 A1 * | 7/1997 |
| JP | 02091043 | 3/1990 |
| JP | 02091043 A * | 3/1990 |
| JP | 9110800 | 4/1997 |

* cited by examiner

*Primary Examiner*—Elvis O. Price
(74) *Attorney, Agent, or Firm*—Michael P. Dilworth

(57) ABSTRACT

A process is disclosed for the production of alkyl salicylic acids wherein the process comprises reacting salicylic acid with an olefin having at least four carbon atoms at elevated temperature in the presence of a perfluoroalkylsulfonic acid, an alkylsulfonic acid, or an acidic clay as a catalyst.

9 Claims, No Drawings

METHOD FOR THE ALKYLATION OF SALICYLIC ACID

I claim the benefit under Title 35, United States Code, § 120 to U.S. Provisional Application No. 60/422,492, filed Oct. 31, 2002, entitled METHOD FOR THE ALKYLATION OF SALICYLIC ACID.

BACKGROUND OF THE INVENTION

1. Field of the Invention

The present invention relates to the alkylation of salicylic acid with long-chain olefins. These alkylated salicylic acids can be overbased to form useful lubricating oil additives.

2. Description of Related Art

It is known to use alkaline earth metal salts of organic carboxylic acids as additives for lubricating oil compositions. These salts have a dispersant property that helps ensure that the insides of engine cylinders remain clean and that deposition of carbonaceous products on pistons and in piston grooves is counteracted, thus preventing piston-ring sticking.

It is also known to prepare basic (or overbased) alkaline earth metal salts of such acids. The overbasing provides an alkaline reserve which, when applied in lubricating oil compositions, reacts with and neutralizes acidic compounds formed during the operation of the engine in which the composition is applied. Hence, any sludge that may arise is dispersed owing to the dispersant property of the salt, while acids that would enhance sludge formation are neutralized.

Overbased salicylates are prepared by overbasing the corresponding alkylated salicylic acids. The alkyl group is typically a long chain alkyl group of greater than about 14 carbon atoms so as to impart oil solubility. Alkylated salicylic acids are conventionally prepared by the alkylation of a phenol to form an alkylphenol followed by carboxylation of the alkylphenol by the Kolbe-Schmitt reaction to provide the alkylated salicyclic acid. In addition to the adverse economics attributable to the use of high temperatures and/or pressures, the Kolbe-Schmitt route to alkylated salicylic acids suffers from the problem that, when substantially linear alkylation feeds are employed, not all of the long-chain alkylphenol is readily carboxylated. Specifically, conventional alkylation of phenol with a substantially linear alkylation feed provides for approximately a 50:50 mixture of ortho-alkylphenol and para-alkylphenol. While the Kolbe-Schmitt reaction readily carboxylates the resulting long chain para-alkylphenol, the resulting long chain ortho-alkylphenol is less reactive and only about 70 percent of total amount of the alkylphenol derived from a substantially linear alkylation feed is typically converted to alkylated salicylic acid during this reaction.

One method of circumventing this problem is to alkylate an alkyl salicylate (e.g., methyl salicylate) and then subject the resulting alkylated alkyl salicylate to hydrolysis so as to provide for the alkylated salicylic acid. Methods of alkylating alkyl salicylates are disclosed in U.S. Pat. No. 5,434,293.

DD-A-269 619 and DD-A-293 108 both disclose the direct alkylation of salicylic acid with an olefin using an acidic ion exchange resin or polyphosphoric acid respectively as catalyst. Both documents teach that the use of sulfuric acid as a catalyst (in prior art processes not involving alkylation of the acid with an olefin) is undesirable because it has many disadvantages, such as corrosion problems and side reactions.

DE 689 600 discloses the use of perchloric acid as the catalyst.

U.S. Pat. No. 1,998,750 discloses the condensation of salicylic acid with any nonaromatic monohydric alcohol having from 5 to 7 carbon atoms, or with compounds capable of furnishing an amyl-, hexyl-, cyclohexyl-, or heptyl- group, in the presence of sulfuric acid.

U.S. Pat. No. 4,810,398 discloses a basic alkaline earth metal salt of a blend of organic carboxylic acids is prepared by (a) preparing a mixture of one equivalent of the blend of organic carboxylic acids and more than one equivalent of an alkaline earth metal hydroxide and/or oxide in a hydrocarbon solvent; (b) introducing carbon dioxide into the mixture obtained in an amount of at least 0.5 equivalent carbon dioxide per equivalent of excess alkaline earth metal; and (c) removing residual solids, if any, and an aqueous layer, if any, whereby the blend of organic carboxylic acids comprises a $C_{8-30}$ alkyl salicylic acid and one or more alkanecarboxylic acids in which the alkyl moiety is branched and has from 4 to 40 carbon atoms. Such a salt has dispersant properties and is said to be suitable for use in lubricating oil and fuel compositions.

U.S. Pat. No. 4,869,837 discloses a process for the preparation of a basic alkaline earth metal salt of a blend of organic carboxylic acids, which comprises (a) preparing a mixture of one equivalent of the blend of organic carboxylic acids and more than one equivalent of an alkaline earth metal hydroxide and/or oxide in a hydrocarbon solvent; (b) introducing carbon dioxide into the mixture obtained in an amount of at least 0.5 equivalent carbon dioxide per equivalent of excess alkaline earth metal; and (c) removing residual solids, if any, and an aqueous layer, if any, whereby the blend of organic carboxylic acids comprises an oil-soluble alkyl salicylic acid and one or more hydrocarbon substituted succinic acids or anhydrides, in which the hydrocarbon radical has a number average molecular weight from 120 to 5000.

U.S. Pat. No. 4,876,020 discloses a lubricating oil composition comprising a lubricating base oil, one or more overbased alkaline earth metal salts of an aromatic carboxylic acid, and a stabilizing agent which has been selected from a polyalkoxylated alcohol having a molecular weight from 150 to 1500.

U.S. Pat. No. 5,049,685 discloses a nuclear substituted salicylic acid represented by the following general formula

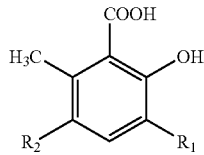

wherein $R_1$ represents a methyl group, an isopropyl group, a tert-butyl group, a tert-amyl group, a tert-hexyl group, a tert-octyl group, an α,α-dialkylbenzyl group or a nuclear substituted α,α-dialkylbenzyl group; and $R_2$ represents a tert-butyl group, a tert-amyl group, a tert-hexyl group, a tert-octyl group, an α,α-dialkylbenzyl group or a nuclear substituted α,α-dialkylbenzyl group) and a salt thereof. The nuclear substituted salicylic acids and salts thereof are said to have good solubility in water, organic solvents or organic polymeric compounds and that they are very favorable as bactericidal and germicidal agents, stabilizers for polymeric compounds or color developing agents for recording materials.

U.S. Pat. No. 5,415,792 discloses overbased alkyl alkyl salicylates that are said to be useful additives for lubricating oil compositions. In particular, the compositions impart detergency and dispersancy to the lubricating oil composition as well as provide for an alkalinity reserve.

U.S. Pat. No. 5,434,293 discloses a method for alkylating alkyl salicylates using a solid acidic alkylation catalyst and approximately equimolar amounts of alkyl salicylate and alkylating feedstock.

U.S. Pat. No. 5,451,331 discloses a process for the production of a lubricating oil additive concentrate having a TBN greater than 300 that comprises reacting, at elevated temperature, component (A) a defined salicylic acid derivative, component (B) an alkaline earth metal base added either in a single addition or in a plurality of additions at intermediate points during the reaction, component (C) at least one compound which is (i) water, (ii) a polyhydric alcohol having 2 to 4 carbon atoms, (iii) a di-($C_3$ or $C_4$) glycol, (iv) a tri-($C_2$–$C_4$) glycol, (iv) a mono- or poly-alkylene glycol alkyl ether of the formula (I) $R(OR^1)_x OR^2$ (I) wherein R is a $C_1$ to $C_6$ alkyl group, $R^1$ is an alkylene group $R^2$ is hydrogen or a $C_1$ to $C_6$ alkyl group and x is an integer from 1 to 6, (vi) a $C_1$ to $C_{20}$ monohydric alcohol, (vii) a $C_1$ to $C_{20}$ ketone, (viii) a $C_1$ to $C_{10}$ carboxylic acid ester, or (ix) a $C_1$ to $C_{20}$ ether, component (D) a lubricating oil, component (E) carbon dioxide added subsequent to the, or each, addition of component (B), component (F) a defined carboxylic acid or derivative, and component (G) at least one compound which is (i) an inorganic halide of (ii) an ammonium alkanoate or mono-, di-, tri- or tetra-alkyl ammonium formate or alkanoate provided that, when component (G) is (ii), component (F) is not an acid chloride, the weight ratios of all components being such as to produce a concentrate having a TBN greater than 300.

U.S. Pat. No. 5,734,078 discloses a process for the production of an alkyl salicylic acid in which the alkyl substituent has at least 6 carbon atoms, comprising reacting salicylic acid with an olefin having at least 6 carbon atoms at elevated temperature in the presence of sulfuric acid as a catalyst. Lubricating oil additives comprising a metal salt of such alkylated salicylic acids and a process for making them are also disclosed.

U.S. Pat. No. 5,792,735 discloses a lubricating oil composition said to be suitable for use in low or medium speed diesel engines that comprises a fuel oil with a residual oil content characterized in that the lubricating oil composition further comprises a hydrocarbyl-substituted phenate concentrate having a TBN greater than 300, and at least one of a hydrocarbyl-substituted salicylate and a hydrocarbyl-substitute sulphonate. The hydrocarbyl-substituted phenate is preferably one modified by incorporation of a carboxylic acid of the formula $RCH(R_1)CO_2H$ where R is a $C_{10}$–$C_{24}$ alkyl group and $R_1$ is hydrogen or a $C_1$ to $C_4$ alkyl group, e.g., stearic acid.

U.S. Pat. No. 6,034,039 discloses complex detergents that are said to provide improved deposit control and corrosion protection in crankcase lubricants.

The disclosures of the foregoing are incorporated herein by reference in their entirety.

SUMMARY OF THE INVENTION

The present invention is directed to the preparation of alkylated salicylic acids from salicylic acid and branched, internal and alpha olefins using a perfluoroalkylsulfonic acid, an alkylsulfonic acid, or an acidic clay, such as Fulcat® 22B or Filtrol® 20X, as the catalyst. It is preferred that the alkyl groups of the sulfonic acids have from 1 to about 30 carbon atoms. Anhydrous methanesulfonic acid (10 to 30 mole % of the moles of salicylic acid) is especially preferred. The conditions are such as to allow a suspension of salicylic acid in the olefin to react at elevated temperatures, preferably from about 120° C. to 160° C., with olefin excesses of up to about 20 mole percent relative to the salicylic acid. The products are mixtures of ortho and para monoalkylated salicylic acids with some dialkylated and trialkylated salicylic acids. The alkyl phenol content is very low and the color of the product is excellent compared to that obtained via the Kolbe-Scmitt synthesis. The alkylated salicylic acids have acid numbers approximately 60–95% of the theoretical value. PDSC and panel coker values of the corresponding overbased calcium salts of the salicylic acids are comparable or superior to control commercial salicylate detergents.

In the preferred case in which methanesulfonic acid is used as the catalyst, the catalyst can be readily removed and recycled by the addition of from about 10 to about 50 weight percent (relative to the reaction mass) of light naphtha to the final reaction product, which precipitates the catalyst. If the catalyst is to be discarded, a water wash can remove the methanesulfonic acid. The solution of alkyl salicylic acid can be used directly for the preparation of overbased alkali or alkaline earth metal salicylates.

More particularly, the present invention is directed to a process for the production of alkyl salicylic acids comprising reacting salicylic acid with an olefin having at least four carbon atoms at elevated temperature in the presence of a perfluoroalkylsulfonic acid, an alkylsulfonic acid, or an acidic clay as a catalyst.

In another aspect, the present invention is directed to composition comprising an alkyl salicylic acid prepared by a process comprising reacting salicylic acid with an olefin having at least four carbon atoms at elevated temperature in the presence of a perfluoroalkylsulfonic acid, an alkylsulfonic acid, or an acidic clay as a catalyst.

DESCRIPTION OF THE PREFERRED EMBODIMENTS

The process of the present invention can be represented by the following equation:

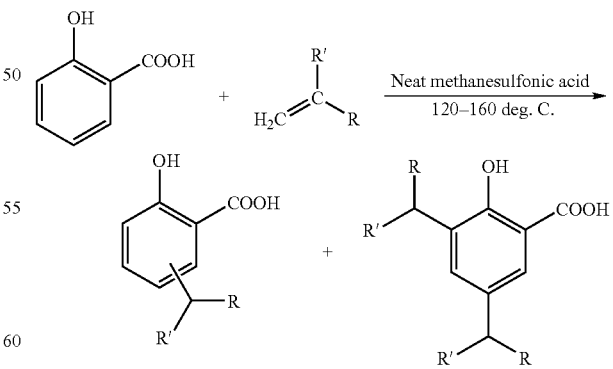

wherein:

R is selected from the group consisting of hydrogen, linear alkyl groups of from 4 to 30 carbon atoms, and branched alkyl groups of from 4 to 30 carbon atoms, and R' is selected from the group consisting of linear alkyl groups of from 4 to 30 carbon atoms and branched alkyl groups of from 4 to 30 carbon atoms.

Both straight-chain and branched-chain olefins, preferably α-olefins, can be employed in the practice of the present invention. Preferably, the olefin has from 4 to 50, more preferably from 8 to 35, and most preferably from 8 to 25 carbon atoms. Suitable olefins include, but are not limited to, isobutylene, propylene trimer, propylene tetramer, 1-hexene, 1-octene, 1-decene, 1-dodecene, 1-tetradecene, 1-hexadecene, 1-octadecene, 1-eicosene, 1-docosene, 1-tetracosene, mixtures of the foregoing, and the like.

Commercial salicylic acid can be employed with or without further purification.

The conditions under which the reaction is carried out depend upon the nature of the olefin to be employed. The conditions to be described hereinafter are for 2-methyl-1-undecene, an example of a longer carbon chain branched 1-olefin. Those skilled in the art will realize that, with other olefins, different optimum reaction conditions may, and probably will, be desirable.

The temperature at which the salicylic acid and the olefin are reacted is preferably about 50° C. or more, and may suitably be in the range from about 50° to about 200° C. The optimum temperature within this range is dependent on the carbon chain length of the olefin. Typically, for a $C_{14}$ olefin the optimum temperature is from about 100° to about 170° C., preferably, about 120° to about 160° C.

The duration of the reaction is usually not critical. A reaction time of from about 2 to about 36 hours is usually satisfactory.

The reaction can, if desired, be carried out in a solvent, but normally no solvent is employed.

The alkyl salicylic acid can be recovered from the reaction mixture by means known in the art. For $C_{12}$ and higher alkyl salicylic acids, solvent extraction, preferably with light naphtha, is typically used.

The alkylated salicylic acids prepared by the process of the present invention are useful as intermediates in the preparation of lubricating oil additives. The method for effecting such use comprises the steps of forming a $C_4$ or higher alkyl salicylic acid as disclosed above, and then reacting it with a metal base in the presence of a solvent at elevated temperature.

The reaction with the metal base can be carried out in the presence of carbon dioxide and, optionally, a carbonation catalyst. The metal base can be an alkali metal or an alkaline earth metal base, or a mixture of the two. An alkaline earth metal base is preferred. Of the alkaline earth metals, calcium, magnesium, and barium are preferred and calcium is especially preferred. The base may take the form of the oxide or the hydroxide, e.g., slaked lime, which is principally calcium hydroxide.

The amount of base added should be sufficient to provide an overbased salt, i.e., one in which the ratio of the number of equivalents of the metal moiety to the number of equivalents of the alkyl salicylic acid moiety is usually greater than about 1.2, and can be as high as 4.5 or greater.

The metal base may be added either in a single addition or in a plurality of additions at intermediate points during the reaction.

The overbasing reaction mixture suitably further contains a promoter, preferably an oxygen-containing organic solvent and optionally water. Suitable promoters include $C_{1-6}$ alcohols, polyhydric alcohols such as glycol, propylene glycol, glycerol, or 1,3-dihydroxypropane, ethers such as $C_{1-4}$ monoethers of glycol or propylene glycol, diisopropyl ether, 1,3- or 1,4-dioxane, or 1,3-dioxolane. Preferably, the promoter is a $C_{1-6}$ alcohol, in particular, methanol.

The solvent for the reaction of the alkyl salicylic acid with the metal base may be
(1) a polyhydric alcohol having 2 to 4 carbon atoms;
(2) a di-($C_2$ to $C_4$) glycol;
(3) a tri-($C_2$ to $C_4$) glycol;
(4) a mono- or polyalkylene glycol alkyl ether of the formula:

$$R^1(OR^2)_xOR^3$$

wherein $R^1$ is a $C_1$ to $C_6$ alkyl group, $R^2$ is an alkylene group, $R^3$ is hydrogen or a $C_1$ to $C_6$ alkyl group and x is an integer from 1 to 6;
(5) a monohydric alcohol having up to 20 carbon atoms;
(6) a ketone having up to 20 carbon atoms;
(7) a carboxylic acid ester having up to 10 carbon atoms;
(8) a volatile liquid hydrocarbon; or
(9) an ether having up to 20 carbon atoms.

The preferred solvent is an inert hydrocarbon, which can be either aliphatic or aromatic. Suitable examples include toluene, xylene, naphtha, and aliphatic paraffins, e.g., hexane, and cycloaliphatic paraffins.

A combination of methanol, which acts as a promoter in the reaction, and naphtha is especially preferred.

In view of the intended use of the overbased product as a lubricating oil additive, it is preferred to incorporate a base oil as a supplemental diluent. The base oil can be an animal oil, a vegetable oil, or a mineral oil. Preferably, it is a petroleum-derived lubricating oil, such as a naphthenic base, a paraffin base, or a mixed base oil. Alternatively, the lubricating oil may be a synthetic oil, for example, a synthetic ester or a polymeric hydrocarbon lubricating oil.

Carbon dioxide is employed in the production of overbased metal salts in the form of a gas or a solid, preferably in the form of a gas, wherein it can be blown through the reaction mixture. Carbon dioxide addition is typically effected after the addition of metal base.

A carbonation catalyst can be used to produce highly overbased metal salts. The catalyst can be either an inorganic compound or an organic compound, preferably an inorganic compound. Suitable inorganic compounds include hydrogen halides, metal halides, ammonium halides, metal alkanoates, ammonium alkanoates or mono-, di-, tri- or tetra-alkyl ammonium formates or alkanoates. Examples of suitable catalysts include calcium chloride, ammonium chloride, calcium acetate, ammonium acetate, zinc acetate, and tetramethyl(ammonium acetate). The catalyst is typically employed at a level of up to about 2% by weight. A more complete description of the production of highly overbased metal alkyl salicylates can be found in EP-A-0351052.

Suitably, the elevated temperature employed in the above reaction may be in the range from about 100° to about 500° F. (about 38° to about 260° C.).

The concentrate of the metal salt in the solvent can be recovered by conventional means, such as distillative stripping. Finally, the concentrate can be filtered, if desired.

The amount of additive concentrate present in the finished lubricating oil will depend on the nature of the final use. For marine lubricating oils, it is typically enough to provide a TBN of from 9 to 100; for automobile engine lubricating oils, enough to provide a TBN of from 4 to 20.

As used herein, the term "Total Base Number" or "TBN" refers to the amount of base equivalent to milligrams of KOH in 1 gram of additive. Thus, higher TBN numbers reflect more alkaline products and therefore a greater alkalinity reserve. The Total Base Number for an additive composition is readily determined by ASTM test method number D2896 or other equivalent methods.

The finished lubricating oil may also contain effective amounts of one or more other types of conventional lubricating oil additives, for example viscosity index improvers, anti-wear agents, antioxidants, dispersants, rust inhibitor, pour-point depressants, and the like.

The advantages and the important features of the present invention will be more apparent from the following examples.

EXAMPLES

Example 1

Alkylation of Salicylic Acid

Salicylic acid (215.0 grams) is added to a 3 liter glass vessel equipped with a stirrer, a thermometer, and a heating mantle. A mixed $C_{14}$–$C_{18}$ olefin (367.7 grams) is added next, followed by an alkylation catalyst, preferably 45.1 grams of methanesulfonic acid. The mixture is heated to 120° C. and kept at that temperature for 24 hours. Next, some light naphtha, such as VM&P naphtha, (582.6 grams) is introduced and the clear solution is allowed to settle to remove the spent catalyst. The product recovered is a clear yellowish naphtha diluted alkyl salicylic acid suitable for direct overbasing or for reaction with previously overbased detergent.

Example 2

Salicylic Acid Monoalkylated with a 16.4:47.9:35.6 Wt/Wt % Mixture of $C_{14}$, $C_{16}$, $C_{18}$ α-olefins A three liter resin kettle was charged with salicylic acid powder (828.96 grams, 6.0 moles). The kettle was fitted with five-hole lid, mechanical stirrer (PTFE bearing, polished glass shaft, PTFE axial and radial turbines), reflux condenser (attached to a nitrogen line and mineral oil bubbler for positive pressure) and mantle, Therm-O-Watch®, thermocouple. The kettle was charged with a commercial mixture of $C_{14}$/$C_{16}$/$C_{18}$ α-olefins (1414.12 grams, 6.30 moles, assuming an average molecular weight of the alkene mixture of 228.11, composition in wt %: 16.4% 1-tetradecene, 47.9% 1-hexadecene, an 35.6% 1-octadecene) and then stirring at about 250–300 rpm was started. Anhydrous methanesulfonic acid (173.47 grams, 1.8 moles, 30 mole % relative to the salicylic acid) was added all at once to the resulting white suspension. The suspension was then heated under nitrogen and stirred to a target pot temperature of 120° C.

As the reaction progressed, the suspension disappeared and became a dark reddish-orange in color. Crystals of what is presumed to be sublimed salicylic acid were present in cool areas of the reaction apparatus. After a total of 25 hours at 120° C., the heating was stopped and the reaction mixture allowed to cool. Light naphtha (1.5 L total) was used to transfer the reaction product from the kettle to a separatory funnel and the phases separated to afford a large upper phase and a dark colored lower phase of spent catalyst. The upper phase was stripped of solvent in vacuo (rotary evaporator, 90° C. water bath, <10 mbar vacuum) over about 2 hours. A brownish oil (2189.77 grams) was obtained, (97.6 % based on the combined weights of the alkene and salicylic acid). This sample was found to have an acid number that was 92% of the theoretical value of 153.20 for a 16.4:47.9:35.6 wt/wt % mixture of monoalkylated salicylic acids.

Example A

Comparative Example

Salicylic Acid Monoalkylated with 80 V/V Aq. Sulfuric Acid with Propylene Tetramer A two liter resin kettle was charged with salicylic acid (138.39 grams, 1.00 mole) and 890 mL (25.6 moles) of an 80% v/v aqueous sulfuric acid solution. The suspension was stirred under a nitrogen positive pressure at 43° C., and then propylene tetramer (185.24 grams, 1.1 moles) was added dropwise over about 0.5 hour. During the addition, the reaction temperature cooled slightly to 41° C. Then, the reaction mixture was warmed to a target temperature of 60° C.; however, there was an exotherm to 75° C. The reaction was kept at about 60° C. for a total of three hours. The deep reddish reaction product was diluted with 600 mL of water and an exotherm, owing to the dilution of the sulfuric acid, occurred. The diluted product separated into two phases, which were treated with 200 mL of n-heptane in a separatory funnel. The upper organic phase was kept and the lower aqueous phase extracted with two 100 mL portions of n-heptane. All of the organic phases were combined and washed twice with 300 mL of water, and then twice with 200 mL of saturated aqueous sodium chloride solution. The organic phase was dried over anhydrous sodium sulfate. Then, the drying agent was removed with suction in a Büchner funnel and the filtrate was stripped in vacuo (90° C. water bath, <20 mbar vacuum) to afford 252.53 grams of a viscous dark reddish oil (78.0% based on the combined weights of the alkene and salicylic acid). The product had a sulfurous odor, and an acid number of 136.0, 74.2% of the theoretical value of 183.1.

Example 3

Salicylic Acid Monoalkylated with Propylene Tetramer and Methanesulfonic Acid

Example 2 was repeated in a two liter resin kettle with 414.99 grams of salicylic acid (3.0 moles), 530.61 grams of propylene tetramer (3.15 moles) and 86.52 grams of methanesulfonic acid (0.90 mole). The mixture was stirred and heated under nitrogen at 120° C. for 26 hours. The reaction product was diluted with 500 mL each of water and n-heptane and the resulting organic phase was washed twice with 500 mL portions of water. The aqueous phases were then combined and extracted with 200 mL of n-heptane. All the organic extracts were combined and then stripped in vacuo (90° C. water bath, <20 mbar vacuum) to afford 868.05 grams of a dark colored viscous oil (92.8% based on the combined weight of propylene tetramer and salicylic acid). The resulting product had an acid number of 163.2 (89.1% of the theoretical value of 183.1).

Example 4

Salicylic Acid Monoalkylated with a 10:10:80 (wt %) Mixture of $C_{14}$, $C_{16}$, $C_{18}$ α-Olefins As in Example 2, salicylic acid (414.34 grams, 3.00 moles), 1-tetradecene (87.32 grams, 0.445 mole), 1-hexadecene (87.34 grams, 0.389 mole), 1-octadecene (698.70 grams, 2.73 moles), and methanesulfonic acid (86.61 grams, 0.90 mole) were combined in a two liter resin kettle. The suspension was warmed at 120° C. for 26.5 hrs. The cooled reaction product was diluted with 600 mL of light naphtha and then filtered with suction through a coarse glass fritted funnel. The filter cake was washed with 300 mL of light naphtha. The filtrate was split in a separatory funnel and the lower dark layer was separated off. The upper organic phase was stripped in vacuo (90° C. water bath, <15 mbar vacuum) to afford 1119.11 grams of a yellowish oil (86.9% based on the combined weights of the alkene and salicylic acid). The alkylation product had an acid value of 133.8 (87.3% of the theoretical value of 147.40).

Example 5

Salicylic Acid Monoalkylated with 10:10:80 Wt % Mixture of 1-Tetradecene, 1-Hexadecene, and 1-Octadecene In a manner similar to Example 2, salicylic acid (829.04 grams, 6.0 moles), 1-tetradecene (152.89 grams, 0.7783 mole), 1-hexadecene (152.81 grams, 0.689 mole), 1-octadecene (1222.60 grams, 5.447 moles), and methanesulfonic acid (173.02 grams, 1.80 moles) were combined in a three liter resin kettle. Under nitrogen, the suspension was brought to 130° C. with stirring and kept at 130° C. for a total of eight hours. The cooled reaction mixture was diluted with 500 mL of n-heptane and the solution was filtered through a coarse glass fritted funnel.

Example 6

Salicylic Acid Monoalkylated with 1-Tetradecene

Example 2 was repeated in a two liter resin kettle with 388.84 grams (2.815 moles) of salicylic acid and 580.49 grams (2.956 moles) of 1-tetradecene with 57.81 grams (0.60 mole) of anhydrous methanesulfonic acid. The suspension was heated and stirred under nitrogen for 24 hours at 120° C. The catalyst was removed by washing the product with one liter of water, followed by stripping at 90° C. under reduced pressure. A dark red-brown oil was obtained (910.66 grams, 93.9% based on the combined weights of alkene and salicylic acid). The resulting product had an acid number of 112.0 (66.8% of the theoretical value of 167.7).

Example 7

Salicylic Acid Monoalkylated with 1-Decene

Example 2 was repeated with 414.72 grams of salicylic acid (3.0 moles), 441.91 grams of 1-decene (3.15 moles) and 86.55 grams of methanesulfonic acid (0.90 mole). The mixture was heated at 120° C. under nitrogen for 24 hours. The resulting product was diluted with 200 mL of light naphtha and then the lower dark colored phase was removed in a separatory funnel. The upper phase was stripped of solvent in vacuo (90° C. water bath, <10 mbar vacuum) to afford 856.6 grams of a dark oil (99.9% based on the combined weights of alkene and salicylic acid). The product had an acid number of 189.8 (94.1% of the theoretical value of 201.5).

Example 8

Salicylic Acid Monoalkylated with 1-Octene

Salicylic acid (414.89 grams, 3.0 moles), 1-octene (353.5 grams, 3.15 moles) and methanesulfonic acid (57.63 grams, 0.60 mole) were combined as in Example 2 in a two liter kettle and warmed to a target temperature of 120° C. under nitrogen positive pressure. The reaction mixture was heated and stirred at 120° C. for a total of 24.5 hours. Light naphtha (200 mL) was added to the reaction product, which was then filtered with suction through a coarse glass fritted funnel. The filtrate split into a larger upper phase and a lower darker phase containing the catalyst. The upper phase was stripped in vacuo (90° C. water bath, <10 mbar vacuum) to provide 755.7 grams of the alkylated salicylic acid as a brown oil (98.4% based on the combined weights of alkene and salicylic acid). The product had an acid number of 211.2 (94.2% of the theoretical value of 224.1).

Example 9

Salicylic Acid Monoalkylated with a Mixture of $C_{20}$, $C_{22}$, and $C_{24}$ α-Olefins Salicylic acid (414.76 grams, 3.0 moles), a blend of $C_{20}$, $C_{22}$, and $C_{24}$ α-olefins (908.82 grams, 3.15 moles), and methanesulfonic acid (86.82 grams, 0.90 mole) were combined as in Example 2 in a two liter resin kettle. As the α-olefin was a waxy solid, the blend was warmed to a 120° C. target temperature under nitrogen without stirring until the olefin became molten, then stirring was begun. The reaction mixture was heated for a total of 22.4 hours at 120° C. The reaction product was diluted with 500 mL of water and 200 mL of n-heptane and the phases split in a separatory funnel. The upper organic phase was washed three times with 300 mL portions of water. Then the organic phase was stripped in vacuo (90° C. water bath, <10 mbar vacuum) to provide 1295.85 grams of a dark colored oil, (97.9 % based on the combined weights of alkene and salicylic acid). This material solidified overnight to a cream colored solid. The product had an acid number of 97.0 (77.6% of the theoretical value of 125.0).

Example 10

Salicylic Acid Monoalkylated with Propylene Trimer (Nonenes)

In a manner similar to Example 2, 414.50 grams (3.00 moles) of salicylic acid, 398.32 grams (3.15 moles) of propylene trimer (nonenes) and 86.67 grams (0.90 mole) of methanesulfonic acid were combined in a two liter resin kettle. The suspension was stirred and warmed at 120° C. for 23 hours under nitrogen positive pressure. The reaction product was allowed to cool, diluted with 300 mL light naphtha. Then the reactor contents were filtered with suction through a coarse fritted glass Büchner funnel and the filtrate was diluted with 500 mL of additional light naphtha and 200 mL of water in a separatory funnel. The upper organic phase was then stripped in vacuo (90° C. water bath, <10 mbar vacuum) to afford 774.88 grams of a dark viscous oil (95.3% based on the combined weights of alkene and salicylic acid). The final alkylate had an acid number of 230.4 (87.4% of the theoretical value of 263.6).

Example 11

Salicylic Acid Monoalkylated with Propylene Pentamer

Salicylic acid (414.41 grams, 3.00 moles), propylene pentamer (662.96 grams, 3.15 moles), and methanesulfonic acid (86.48 grams, 0.90 mole) were combined as in Example 2 in a two liter resin kettle. The suspension was warmed at 120° C. for a total of 23 hours under nitrogen. The cooled, dark reaction product was diluted with 500 mL of n-heptane and then filtered through a coarse glass fritted Büchner funnel with suction. The filtrate was a two-phase system. The lower, catalyst, phase was separated off and the upper organic phase stripped in vacuo (90° C. water bath, about 30 mbar vacuum) to afford 1065.74 grams of a viscous dark oil (98.9% yield based on the combined weights of alkene and salicylic acid). The product of the alkylation had an acid number of 158.6 (98.5% of the theoretical value of 161.0).

In view of the many changes and modifications that can be made without departing from principles underlying the invention, reference should be made to the appended claims for an understanding of the scope of the protection to be afforded the invention.

What is claimed is:

1. A process for the production of alkyl salicylic acids comprising reacting salicylic acid with an olefin having at least four carbon atoms at an elevated temperature in the range of from about 50° C. to about 200° C. in the presence of a perfluoroalkylsulfonic acid, an alkylsulfonic acid, or an acidic clay as a catalyst.

2. The process of claim 1 wherein the catalyst is anhydrous methanesulfonic acid.

3. The process of claim 1 wherein the olefin is selected from the group consisting of isobutylene, propylene trimer, propylene tetramer, 1-hexene, 1-octene, 1-decene, 1-dodecene, 1-tetradecene, 1-hexadecene, 1-octadecene, 1-eicosene, 1-docosene, 1-tetracosene, and mixtures of the foregoing.

4. The process of claim 2 wherein the olefin is selected from the group consisting of isobutylene, propylene trimer, propylene tetramer, 1-hexene, 1-octene, 1-decene, 1-dodecene, 1-tetradecene, 1-hexadecene, 1-octadecene, 1-eicosene, 1-docosene, 1-tetracosene, and mixtures of the foregoing.

5. The process of claim 1 wherein said elevated temperature is in the range of from about 120° to about 160° C.

6. The method of claim 1 wherein the olefin comprises a mixture of $C_{14}$–$C_{18}$ α-olefins.

7. The method of claim 1 wherein the olefin comprises a blend of $C_{20}$, $C_{22}$, and $C_{24}$ α-olefins.

8. The method of claim 1 wherein the olefin comprises propylene pentamer.

9. The method of claim 1 wherein the olefin comprises 2-methyl-1-undecene.

* * * * *